(12) United States Patent
Coates

(10) Patent No.: US 8,220,462 B2
(45) Date of Patent: *Jul. 17, 2012

(54) CUFFED MEDICAL TUBES

(75) Inventor: Daniel Jay Coates, Ogden Dunes, IN (US)

(73) Assignee: Smiths Group PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,406

(22) Filed: Mar. 2, 2012

(65) Prior Publication Data

US 2012/0152257 A1 Jun. 21, 2012

Related U.S. Application Data

(63) Continuation of application No. 12/448,409, filed as application No. PCT/GB2007/004879 on Dec. 19, 2007.

(30) Foreign Application Priority Data

Jan. 3, 2007 (GB) .................................. 0700045.8

(51) Int. Cl.
*A61M 16/00* (2006.01)
(52) U.S. Cl. ............... 128/207.14; 604/509; 604/96.01
(58) Field of Classification Search ........ 128/207.14–207.16; 604/509, 604/96.01, 99.01–99.03, 103.06–103.08
See application file for complete search history.

(56) References Cited

U.S. PATENT DOCUMENTS

| | | | | |
|---|---|---|---|---|
| 3,565,079 A | * | 2/1971 | Jackson | 128/207.15 |
| 3,734,100 A | * | 5/1973 | Walker et al. | 128/207.15 |
| 3,810,474 A | | 5/1974 | Cross | |
| 3,812,860 A | | 5/1974 | Gilbert et al. | |
| 4,693,243 A | | 9/1987 | Buras | |
| 5,251,619 A | | 10/1993 | Lee | |
| 5,653,229 A | | 8/1997 | Greenberg | |
| 7,293,561 B2 | * | 11/2007 | Madsen et al. | 128/207.14 |
| 2003/0136413 A1 | * | 7/2003 | Brain et al. | 128/207.15 |
| 2004/0221853 A1 | | 11/2004 | Miller | |
| 2008/0000482 A1 | | 1/2008 | Maguire | |

FOREIGN PATENT DOCUMENTS

| | | |
|---|---|---|
| EP | 0586717 | 3/1994 |
| EP | 0 884 061 | 12/1998 |
| EP | 1103280 | 5/2001 |
| GB | 1178813 | 1/1970 |
| GB | 2329841 | 4/1999 |
| GB | 2335362 | 9/1999 |
| JP | 11-9694 | 1/1999 |

* cited by examiner

*Primary Examiner* — Lynne Anderson
(74) *Attorney, Agent, or Firm* — Louis Woo

(57) ABSTRACT

A cuffed silicone tracheostomy tube has two tapered recesses 17 and 18 on its outer surface in which opposite ends 7 and 8 of a resilient cuff 6 are bonded using an adhesive or solvent. Two shallow ribs 22 and 23 extend around the tube on the inner edge of each recess 17 and 18, projecting outwardly to prevent the adhesive or solvent spreading onto the inflatable portion 10 of the cuff 6. The cuff 6 has several shallow ribs 9 extending around the cuff and spaced along its inflatable portion 10 to promote even inflation.

22 Claims, 2 Drawing Sheets

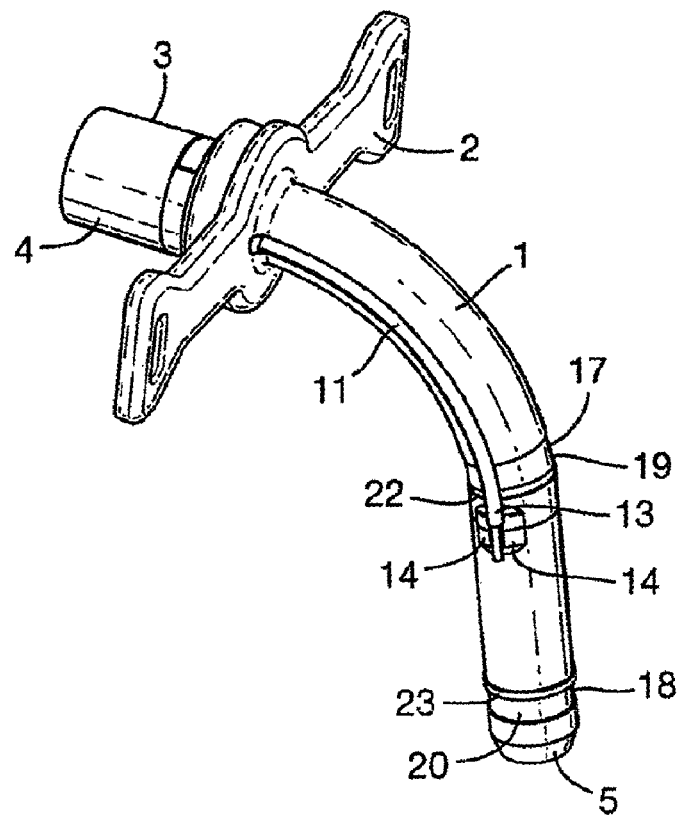
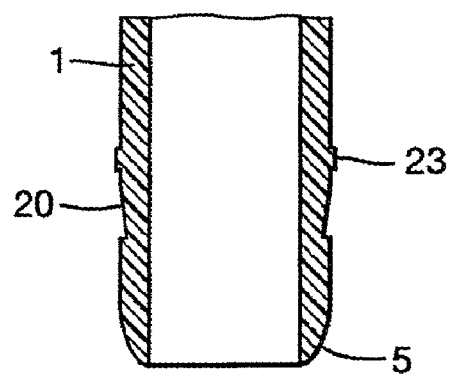

CUFFED MEDICAL TUBES

CROSS REFERENCE TO RELATED APPLICATIONS

This application is a continuation of U.S. application Ser. No. 12/448,409 having a filing date of Jun. 19, 2009 based on PCT application No. PCT/GB2007/004879 filed on Dec. 19, 2007, and claims priority from GB application No. 0700045.8 filed on Jan. 3, 2007.

FIELD OF INVENTION

This invention relates to cuffed medical tubes of the kind having a tubular shaft and an inflatable sealing cuff extending coaxially along a part of the shaft, the opposite ends of the cuff being attached with the shaft by an adhesive or solvent in respective annular attachment regions of the shaft.

The invention is more particularly, but not exclusively, concerned with cuffed tracheal tubes.

BACKGROUND OF INVENTION

It is common practice for tracheal tubes to have an inflatable sealing cuff towards their patient, distal end. The cuff is deflated so that it lies close to the wall of the tube during insertion and is then inflated via an inflation line so that the cuff expands and contacts the wall of the trachea to provide a seal with patient tissue. In this way, passage of gas along the trachea is confined to flow along the bore of the tube.

The cuffs are of tubular shape extending coaxially along the tube and are attached at opposite ends, or collars, to the outside wall of the tracheal tube shaft. The attachment is typically achieved by means of a solvent or adhesive applied between the collar and the wall of the shaft, or by thermal bonding. These methods of attachment work well with tubes made of PVC and some other plastics but there can be difficulties with cuffs made of silicone or other highly elastic material where these are arranged to be a tight fit on the shaft when deflated. In such cuffs there is a tendency for the cuff-bonding adhesive to seep from the cuff region towards the region that is intended to be inflatable. This can lead to a poorly-defined attachment border and an irregular shape when inflated. Also, the longer cure time of some adhesives may make it more difficult to form a good join.

It is an object of the present invention to provide an alternative cuffed medical tube and a method of manufacture of a cuffed medical tube.

According to one aspect of the present invention there is provided a cuffed medical tube of the above-specified kind, characterised in that each attachment region has a raised annular rib projecting above the surface of the shaft at inner ends of the respective regions to restrict flow of adhesive or solvent beyond the attachment regions and onto the inflatable portion of the cuff.

BRIEF DESCRIPTION OF INVENTION

The attachment region towards the patient end preferably includes a recess in which an end of the cuff is attached and preferably, both attachment regions include a recess in which a respective end of the cuff is attached. The or each recess preferably slopes to provide a frusto-conical surface that is deeper towards the or each end of the cuff. Preferably, both recesses slope to provide frusto-conical surfaces, the recesses inclining in opposite senses. The depth of the or each recess at one end is preferably substantially the same as the thickness of the cuff such that there is a substantially stepless transition between the surface of the shaft and the surface of the cuff. The cuff is preferably of a resilient material and is arranged so that its inflatable portion closely embraces the shaft when deflated. The shaft and cuff are preferably of a silicone material. The cuff may have a plurality of shallow annular ribs on its inner surface spaced from one another along the inflatable portion.

According to another aspect of the present invention there is provided a method of manufacture of a cuffed medical tube including the steps of providing a tubular shaft having two annular attachment regions spaced from one another along the shaft and bounded by respective annular ribs projecting above the surface of the shaft at the ends of the regions closer to one another, providing an inflatable sealing cuff that is a close fit on the shaft at least at opposite ends of the cuff, applying an adhesive or solvent to the attachment regions, and applying the cuff to the shaft such that opposite ends of the cuff locate on the attachment regions and are bonded thereto by the adhesive or solvent to leave an inflatable region of the cuff between the bonded ends.

According to a further aspect of the present invention there is provided a cuffed medical tube having a tubular shaft and an inflatable sealing cuff extending coaxially along a part of the shaft and attached with the shaft at opposite ends, the cuff being of a resilient material and closely embracing the shaft along its entire length when deflated, characterised in that the cuff has a plurality of annular ribs spaced from one another along the length of the cuff on the inner surface of its inflatable portion and adapted to promote even inflation of the cuff.

BRIEF DESCRIPTION OF DRAWINGS

A tracheostomy tube and its method of manufacture will now be described, by way of example, with reference to the accompanying drawings, in which:

FIG. 2 is a perspective view of the tube with the cuff removed; and

FIG. 3 is an enlarged cross-sectional view of the patient end of the tube with the cuff omitted.

DETAILED DESCRIPTION OF INVENTION

Figure 1:
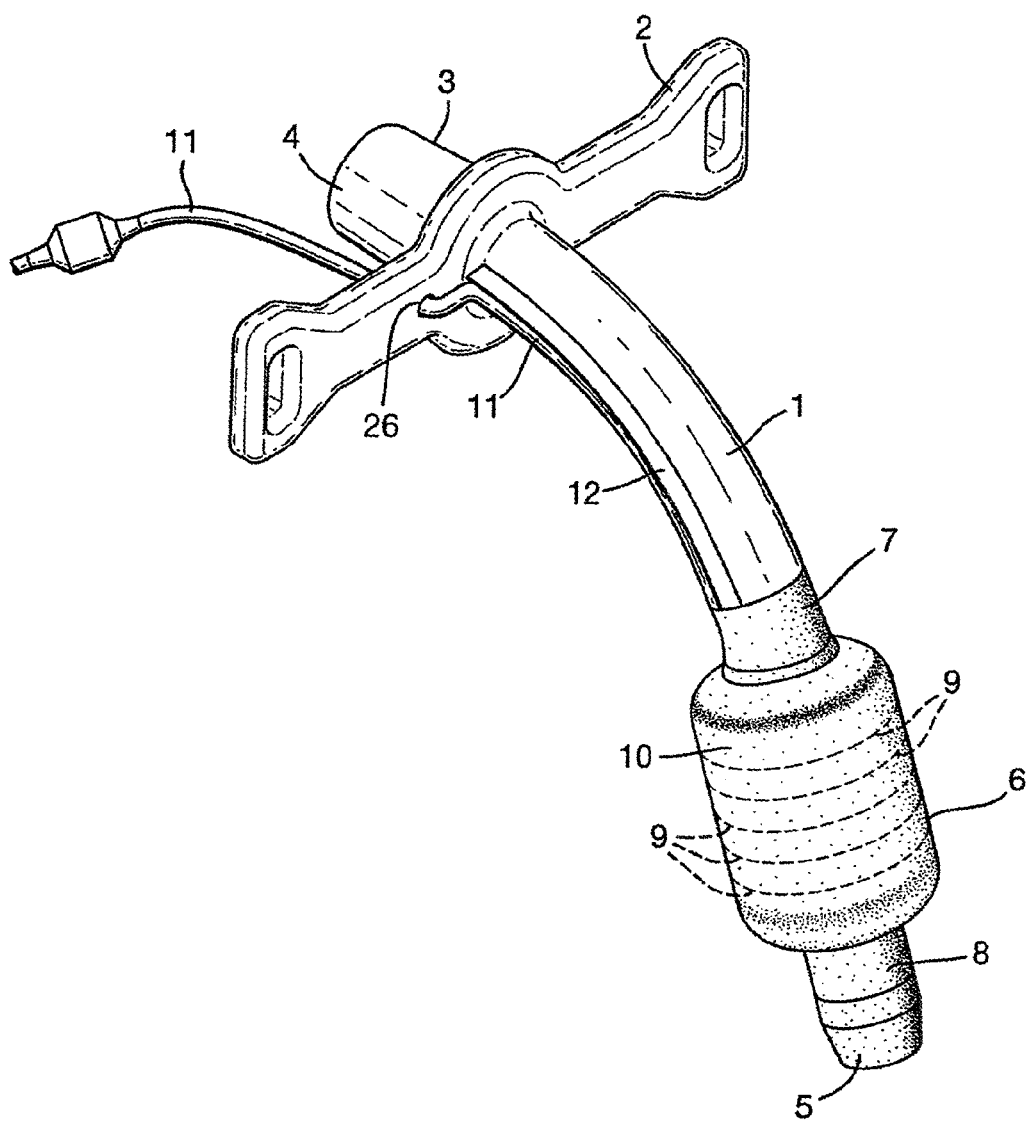
FIG. 1 is a perspective view of the tube with the cuff inflated.

The tube comprises a curved tubular shaft 1 with a flange 2, close to the machine end 3, by which the tube is retained in position in a tracheostomy. A cylindrical coupling 4 is attached with the shaft 1 and projects from the machine side of the flange 2. Close to its opposite, patient end 5, a tubular sealing cuff 6 is attached at opposite end collars 7 and 8 with the outer surface of the shaft 1. The cuff 6, shaft 1 and flange 2 are all moulded of a relatively soft silicone material. In its natural, deflated state the cuff 6 is substantially cylindrical, lying close to the surface of the shaft 1. The cuff 6 has several shallow, internal annular ribs 9 spaced from one another along its central inflatable portion 10, the purpose of which will be explained later. A small bore inflation line 11 extends along the tube bonded into a moulded channel 12 along the shaft 1. The inflation line 11 extends along one side of the shaft 1, that is, displaced by 90° from the plane of curvature of the shaft. The inflation line 11 extends beneath the machine end collar 7 of the cuff 6; its machine end 13 is terminated beneath the inflatable portion 10, being retained between two shallow wedge-shape projections 14 (FIG. 2). These projections 14 act as an anti-occlusion feature to prevent the cuff 6 valving closed the end 13 of the inflation line 11 and also protect the cuff from damage by the end of the inflation line.

The two collars 7 and 8 of the cuff 6 are secured with the outer surface of the shaft 1 in respective attachment regions 17 and 18 (FIGS. 2 and 3). These regions 17 and 18 are provided by shallow annular recess 19 and 20 in the surface of the shaft 1. The recesses 19 and 20 each slope to form frusto-conical surfaces, being deeper at their outer ends and being level with the shaft surface at their inner ends, as shown most clearly in FIG. 3. In this way, it can be seen that the ends of the collars 7 and 8 on the cuff 6 locate at the deeper end of the recesses 19 and 20 respectively. The depth of the recesses 19 and 20 at their deeper ends is about 0.38 mm, which is substantially the same as the thickness of the cuff material allowing for a thickness of adhesive used to bond the cuff collars 7 and 8 to the shaft 1. In this way, there is a stepless transition between the surface of the shaft 1 and the surface of the cuff 6 at both ends.

The shaft 1 has a further surface feature in the form of two shallow annular ribs 22 and 23 located at the inner end of each recess 19 and 20, that is, at the ends of the recesses closer to one another. The ribs 22 and 23 project by about 0.2 mm above the surface of the shaft 1 and serve as dams to restrict flow of adhesive or solvent out of the recesses 19 and 20 and inwardly of the cuff 6.

The tube is manufactured by moulding the shaft 1 and flange 2 from silicone as a single piece about the coupling 4, which is of a harder material. An adhesive is applied to the inflation line channel 12 and the inflation line 11 is threaded through a hole 26 in the flange 2 and then laid into the channel so that its patient end 13 locates between the two wedge-shape projections 14. Adhesive is then applied around the two recesses 19 and 20 and the cuff 6 is loaded onto the shaft 1 so that its end collars 7 and 8 locate in the recesses. It will be appreciated that the adhesive or solvent could be applied to the inner surface of the collars 7 and 8 instead of directly to the recesses 19 and 20. The shape and resilient nature of the cuff 6 are such that the cuff closely and tightly embraces the surface of the shaft 1 along its entire length when deflated. Without the ribs 22 and 23 there would be a tendency for adhesive in the recesses 19 and 20 to wick between the inside surface of the cuff 6 and the shaft surface and flow outside the recesses. This would lead to an uneven boundary of the bonded regions, which in turn would lead to a distorted shape of the inflatable portion 10 when inflated. The problem is made worse because of the relatively long cure times of adhesives used with silicone, which makes it more difficult to attach one collar at a time to the shaft. The frusto-conical shape to the recesses 19 and 20, however, ensures that there is a smooth, stepless transition between the outside surface of the shaft 1 and the cuff 6 where they meet and also ensures that the cuff can lie in intimate contact with the surface of the recesses along a greater part of their length than would be the case with a recess of cylindrical shape. The taper in the recesses 19 and 20 also helps make the external surface of the tube smoother in the region of the ribs 22 and 23. The smooth surface presented in the transition regions at opposite ends of the cuff 6 facilitates atraumatic insertion and removal through a tracheostomy opening. This is more important at the patient end of the cuff 6, for insertion, than at the machine end of the cuff, so it would be possible to use a conventional join at the machine end if desired although preferably, both ends are attached in the same manner.

To inflate the cuff 6, air is supplied via the inflation line 11, such as by a syringe (not shown) so that it flows out at its machine end 13 into the potential space between the cuff 6 and the outside of the shaft 1. The ribs 9 around the inside of the cuff 6 channel the air to flow initially around the tube in an annular channel defined between adjacent ribs on either side of the machine end 13 of the inflation line 11. As pressure increases, these ribs 9 lift away from the surface of the shaft 1 to allow air to flow into the adjacent channels and so on. This ensures that the cuff 6 inflates symmetrically.

The invention could be used with other cuffed medical tubes and is not confined to tracheal tubes. The tubes could be reinforced with a helical reinforcement member, such as a wire. Although the invention has particular advantages with silicone tubes, it could be used with tubes of various different plastics. The ribs on the inside of the cuff may be used without the ribs on the shaft or the ribs on the shaft may be used without the ribs on the cuff.

The invention claimed is:

1. A cuffed medical tube, comprising:
    a tubular shaft having a machine end and a patient end, the shaft including spaced apart annular attachment regions close to the patient end of the shaft, the shaft having a constant outer diameter except at the attachment regions, corresponding annular projections each having a diameter larger than the outer diameter of the shaft rising above the outer surface of the shaft at the respective ends of the annular attachment regions that are closer to each other; and
    an inflatable sealing cuff having opposite end collars extending coaxially along at least a part of the shaft that includes the annular attachment regions;
    wherein the end collars of the cuff are attached to the respective annular attachment regions of the shaft by an adhesive or solvent applied to the respective annular attachment regions so that an inflatable portion of the cuff is formed between the annular attachment regions; and
    wherein the corresponding annular projections above the surface of the shaft at the inner ends of the respective attachment regions restrict flow of the adhesive or solvent from the respective attachment regions to the inflatable portion of the cuff.

2. The cuffed medical tube according to claim 1, wherein at least the attachment region towards the patient end includes an annular recess around which the adhesive or solvent is applied to attach one of the end collars of the cuff to the shaft.

3. The cuffed medical tube according to claim 1, further comprising corresponding annular recesses formed about the attachment regions, the adhesive or solvent being applied to the annular recesses to attach the end collars of the cuff to the shaft.

4. The cuffed medical tube of claim 3, wherein each of the projections comprises an annular rib that projects above the surface of the shaft and serves as a dam to restrict flow of the adhesive or solvent from a corresponding one of the annular recesses.

5. The cuffed medical tube according to claim 3, wherein each of the recesses slopes to provide a frusto-conical surface that is deeper towards the end of the corresponding end collar attached to the shaft by the adhesive or solvent in said each recess.

6. The cuffed medical tube according to claim 1, wherein the shaft and cuff are made of a soft silicone material; and
    wherein the machine end has a coupling made of a material harder than the silicone material.

7. The cuffed medical tube according to claim 1, wherein the cuff is of a resilient material and is arranged so that its inflatable portion closely embraces the shaft when deflated.

8. The cuffed medical tube according to claim 3, wherein the tube is a tracheostomy tube.

9. The cuffed medical tube of claim 1, further comprising a flange close to the machine end of the shaft and an inflation line that extends along the shaft with its air outflow end terminated beneath the inflatable portion of the cuff.

10. The cuffed medical tube of claim 9, wherein the inflation line is extended along the outside of the shaft.

11. A tracheostomy tube, comprising:
   a tubular shaft having a machine end and a patient end, the shaft including spaced apart annular recesses at a portion of the shaft that is closer to the patient end than the machine end, the shaft further having a surface feature in the form of annular projections rising above the outer surface of the shaft at the respective ends of the annular recesses that are closer to each other, an adhesive or solvent applied around the respective annular recesses; and
   an inflatable sealing cuff extending coaxially along at least a part of the shaft that includes the annular recesses, the cuff being attached to the shaft by the adhesive or solvent around the annular recesses to form an inflatable portion of the cuff that extends along the shaft between the annular projections;
   wherein the annular projections rising above the surface of the shaft at the inner ends of the annular recesses restrict flow of the adhesive or solvent from the recesses to the inflatable portion.

12. The tracheostomy tube of claim 11, wherein each of the projections comprises an annular rib that projects above the surface of the shaft and serves as a dam to restrict flow of the adhesive or solvent from a corresponding one of the annular recesses.

13. The tracheostomy tube of claim 11, wherein the cuff is made of a resilient material and is of a shape such that the inflatable portion closely embraces the shaft when deflated.

14. The tracheostomy tube according to claim 11, wherein each of the recesses slopes to provide a frusto-conical surface that is deeper away from the annular projection that serves as a dam to said each recess.

15. The tracheostomy tube according to claim 11, wherein the shaft and cuff each are made of a soft silicone material.

16. The tracheostomy tube of claim 11, further comprising a flange close to the machine end of the shaft and an inflation line that extends along one side of the shaft with its air outflow end terminated beneath the inflatable portion of the cuff.

17. A method of manufacturing a cuffed medical tube, comprising the steps of:
   a) providing a tubular shaft to include
      a machine end and a patient end,
      spaced apart annular attachment regions closer to the patient end than the machine end, and
      corresponding annular projections rising above the outer surface of the shaft at the respective ends of the annular attachment regions that are closer to each other;
      wherein the shaft has a constant outer diameter except at the attachment regions and the corresponding annular projections each have a diameter larger than the outer diameter of the shaft;
   b) providing an inflatable sealing cuff adapted to have a close fit about the shaft;
   c) applying an adhesive or solvent to the attachment regions of the shaft; and
   d) extending the cuff coaxially along at least the part of the shaft that includes the annular attachment regions so that the cuff is attached respectively to the annular attachment regions to thereby provide an inflatable portion of the cuff between the annular projections coaxially along the shaft, the annular projections restricting flow of the adhesive or solvent from the attachment regions to the inflatable portion of the cuff.

18. The method of claim 17, wherein the step a further comprises the step of forming corresponding annular recesses about the attachment regions; and
   wherein the step c further comprises the step of applying the adhesive or solvent around the annular recesses.

19. The method of claim 18, wherein annular recesses are respectively formed about the attachment regions; and wherein the step a further comprises the step of forming each of the projections as an annular rib that projects above the surface of the shaft to serve as a dam to restrict flow of the adhesive or solvent from a corresponding one of the annular recesses to the inflatable portion.

20. The method of claim 17, further comprising the step of forming each of the recesses to have a slope to provide a frusto-conical surface that is deeper away from its corresponding annular rib.

21. The method of claim 17, further comprising the steps of:
   making the shaft and the cuff from a soft silicone material; and
   arranging the cuff to closely embrace the shaft when it is deflated.

22. The method of claim 17, wherein the cuffed medical tube is a tracheostomy tube, the method further comprising the steps of:
   providing a flange close to the machine end of the shaft; and
   providing an inflation line that extends along one side of the shaft with its air outflow end terminated beneath the inflatable portion of the cuff.

* * * * *

UNITED STATES PATENT AND TRADEMARK OFFICE
CERTIFICATE OF CORRECTION

PATENT NO. : 8,220,462 B2
APPLICATION NO. : 13/410406
DATED : July 17, 2012
INVENTOR(S) : Daniel Jay Coates It is certified that error appears in the above-identified patent and that said Letters Patent is hereby corrected as shown below:

In the Claims:

Col. 6, line 25, Claim 19, change "18" to --17--.

Col. 6, line 32, Claim 20, change "17" to --18--.

Signed and Sealed this
Sixteenth Day of April, 2013

Teresa Stanek Rea
*Acting Director of the United States Patent and Trademark Office*